(12) United States Patent
Driver, Jr.

(10) Patent No.: US 6,837,862 B2
(45) Date of Patent: Jan. 4, 2005

(54) BREAKAWAY LEG SLING

(76) Inventor: John Allen Driver, Jr., 212 Sheffield Way, Warner Robins, GA (US) 31088

( * ) Notice: Subject to any disclaimer, the term of this patent is extended or adjusted under 35 U.S.C. 154(b) by 363 days.

(21) Appl. No.: 10/058,584

(22) Filed: Jan. 28, 2002

(65) Prior Publication Data

US 2002/0183670 A1 Dec. 5, 2002

Related U.S. Application Data

(63) Continuation-in-part of application No. 09/866,818, filed on May 29, 2001.

(51) Int. Cl.[7] .................................................. A61F 5/00
(52) U.S. Cl. .............................. 602/4; 602/23; 602/27; 128/875; 128/882
(58) Field of Search ............................... 602/4, 23, 27, 602/28; 128/875, 882; 135/65, 66, 68

(56) References Cited

U.S. PATENT DOCUMENTS

| | | | | |
|---|---|---|---|---|
| 1,608,032 A | * | 11/1926 | McNabb | 602/30 |
| 1,660,721 A | | 2/1928 | Schrag | 602/16 |
| 2,543,847 A | | 3/1951 | Hallstedt | 602/4 |
| 2,573,866 A | | 11/1951 | Murphy | 602/16 |
| 2,654,365 A | | 10/1953 | Whitaker | 602/16 |
| 3,739,772 A | | 6/1973 | Ennis | 602/4 |
| 4,430,990 A | | 2/1984 | Whitehead | 601/45 |
| 4,483,336 A | | 11/1984 | Deitch | 602/4 |
| 4,628,925 A | * | 12/1986 | Witzel | 128/878 |
| 4,793,370 A | * | 12/1988 | Perez et al. | 135/69 |
| 4,823,782 A | | 4/1989 | Powlan | 602/4 |
| 4,913,136 A | | 4/1990 | Chong | 602/24 |
| 5,020,790 A | | 6/1991 | Beard | 482/4 |
| 5,101,815 A | | 4/1992 | Langdom-Orr et al. | 602/12 |
| 5,172,703 A | | 12/1992 | Tiede | 128/875 |
| 5,348,035 A | * | 9/1994 | Porter | 135/66 |
| 5,564,131 A | | 10/1996 | Anscher | 2/340 |
| D377,833 S | * | 2/1997 | Schwartz | D24/190 |
| 5,630,258 A | | 5/1997 | Schneider | 24/303 |
| 5,643,184 A | | 7/1997 | Toso | 602/19 |
| 5,779,655 A | | 7/1998 | Holden | 602/5 |
| 5,860,944 A | | 1/1999 | Hoffman, Jr. | 602/19 |
| 5,882,321 A | | 3/1999 | Fisk | 602/4 |
| 5,911,696 A | | 6/1999 | Coates | 602/4 |
| 5,983,464 A | | 11/1999 | Bauer | 24/303 |
| 6,098,384 A | | 8/2000 | Porrello | 54/36 |
| 6,163,938 A | | 12/2000 | Weber-Unger | 24/303 |
| 6,428,495 B1 | * | 8/2002 | Lynott | 602/23 |
| 2003/0098051 A1 | * | 5/2003 | Fismer | 135/66 |

* cited by examiner

Primary Examiner—Henry Bennett
Assistant Examiner—Amanda Flynn

(57) ABSTRACT

The Breakaway Leg Sling is provided for use with a walker or crutches and suspends a single leg in a below-the-knee cast, shoe, or bandaged foot in a rearward, elevated position and assists the patient with weight avoidance on the suspended leg. The apparatus is prepared for use from a safe sitting position, and the leg is placed into its suspended position during the natural motion of standing. If needed, the apparatus includes a breakaway safety fastener that disengages at an effective, pre-determined force using the muscles of the suspended leg thereby providing the patient with immediate use of the suspended leg to regain balance and prevent a potential fall. If disengaged, the safety fastener is easily restored to operational use. The Breakaway Leg Sling is comprised of a torso harness device, a detachable foot cradle device, a load strap used to engage the torso harness to the foot cradle device, and the breakaway safety fastener incorporated into the length of the load strap. The foot cradle device may be left on the foot for extended periods of time without hampering the patient's comfort thereby leaving the foot cradle anchor in a ready-to-connect position. If desired, the foot cradle device may be removed for bathing or other purposes, and the foot cradle device will retain its custom size thus saving the patient time and effort when replacing the foot cradle device on the foot or cast.

7 Claims, 4 Drawing Sheets

FIG. 1
FIG. 2
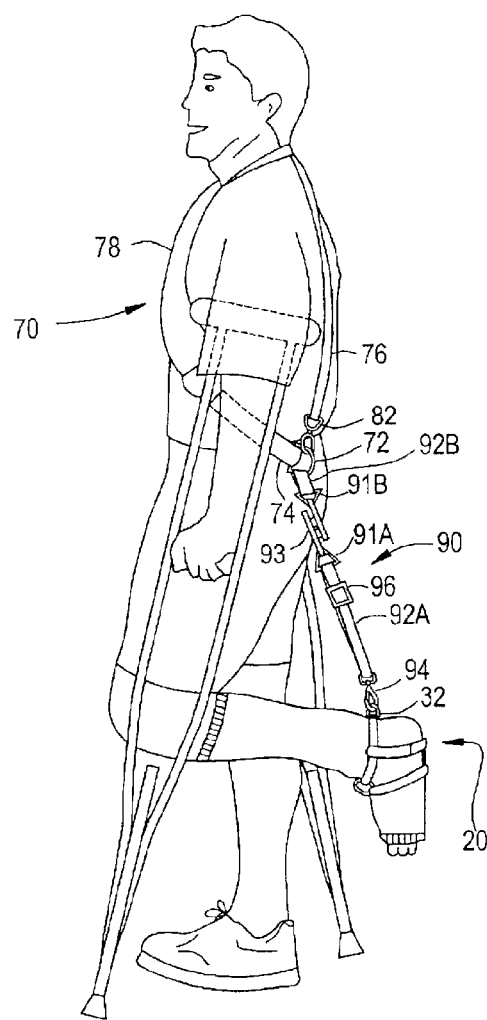
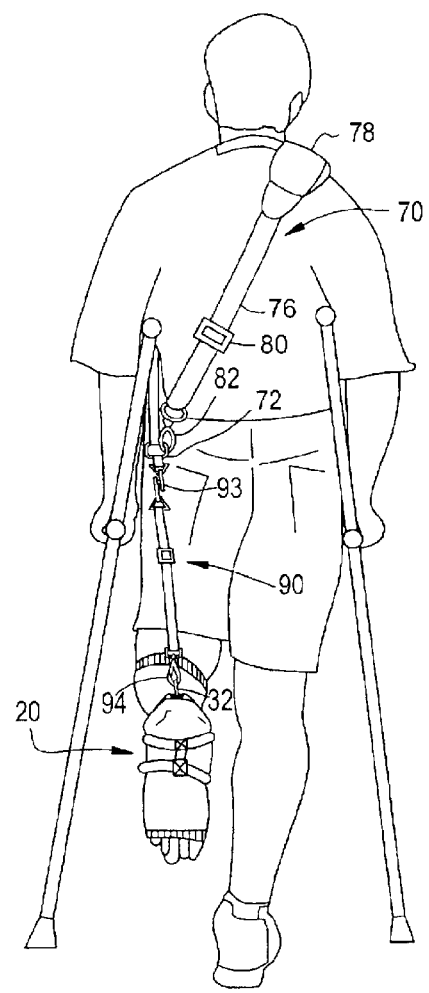

FIG. 3
FIG. 4
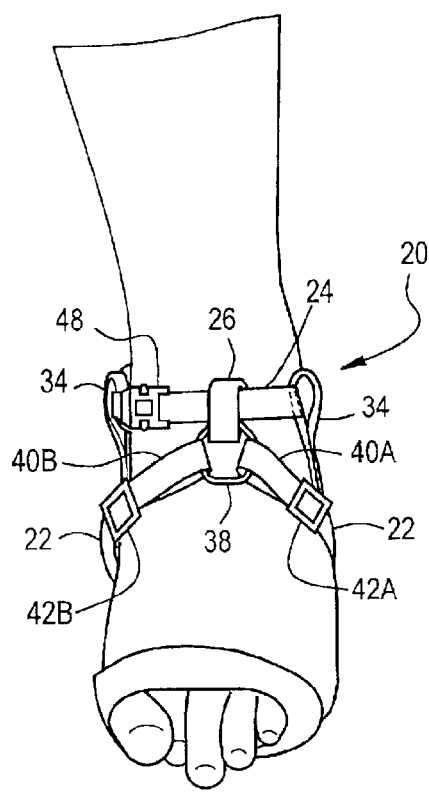
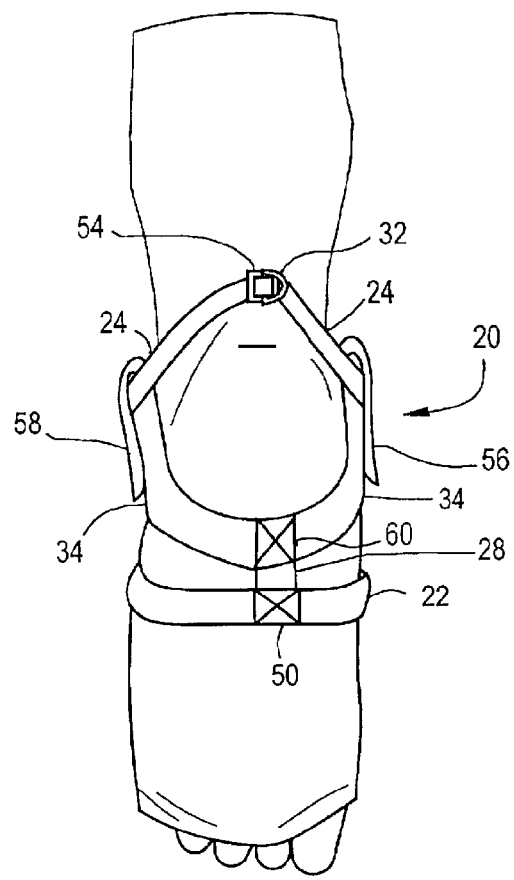

BREAKAWAY LEG SLING

CROSS-REFERENCE TO RELATED APPLICATIONS

This application is a continuation-in-part of, and claims benefit of, co-pending U.S. application Ser. No. 09/866,818, filed May 29, 2001, entitled, "Ambulatory Leg Suspensory Apparatus."

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Whenever a doctor prescribes a period with limited or no weight bearing on a single leg or foot, in order to avoid pain or improve healing, the present invention provides an appliance to support the single leg of a patient in a rearward, suspended state while standing on the patient's other leg. This appliance assists the patient in the prevention of weight bearing. The appliance is designed for use with a below-the-knee cast, a similar strap-on orthopedic boot, an orthopedic shoe, a tennis shoe, or a bandaged foot. The appliance transfers the load of the suspended leg onto the patient's upper torso and is designed to work in conjunction with a walker or crutches. If the patient loses balance, the appliance includes a breakaway safety fastener designed to open at a pre-determined force. If necessary the patient can use the muscles of the suspended leg to disengage the sling at the breakaway safety fastener, which provides the patient with immediate use of the injured leg to regain balance. Afterward, the safety fastener is easily restored to operational use.

As discussed in U.S. Pat. No. 5,882,321, Leg Sling and Abdominal Belt, Fisk (1999), few ambulatory leg slings exist of a prior art. However, an ambulatory leg sling providing a means to disengage and provide the patient immediate use of the injured leg to regain balance has not been disclosed or suggested in the prior art. The Breakaway Leg Sling incorporating the breakaway safety fastener accomplishes this feat. U.S. Pat. No. 2,543,847, Leg sling For Treatment of Unilateral Leg Diseases, Halstedt (1951), disclosed an ambulatory leg sling for use with crutches and provided for suspension of a single leg in a rearward, elevated position. U.S. Pat. No. 2,543,847 was designed to treat a special type of disease, specifically Legg-Perthes disease. In the treatment of this disease, the patient does not wear a cast on the foot and leg but must avoid weight bearing. Mr. Halstedt did not design the Leg Sling For Treatment of Unilateral Leg Diseases to securely, safely encase and ergonomically interface with a below-the-knee cast but rather interface only with the patient's shoe; this leg sling does not provide a slip free and secure means of encasement for the below-the-knee cast. And, if the patient loses balance while using the Leg Sling For Treatment of Unilateral Leg Diseases, the patient might trip and incur additional injury. As a result, the Halstedt leg sling has not been adopted by the medical community as a means to avoid weight bearing on the foot or ankle healing in a below-the-knee cast or soft orthopedic shoe.

U.S. Pat. No. 2,543,847 utilized a single strap with two terminal ends. One terminal end was attached to a single buckle, and the free end of the strap passed through the same buckle twice more to fashion two loops. One loop was placed over the shoulder of the patient on the side opposite of the suspended leg, and the shank of the leg rested in the bottom of the second U-shaped loop thereby providing a means of suspending the leg. U.S. Pat. No. 2,543,847 had several limitations. First, during gait, the U-shaped loop had a tendency to slip along the shank of the leg. Although arm slings successfully used the U-shaped loop as the suspensory means, the U-shaped loop was less effective for suspending the leg because the leg cannot be held as stationary during motion. If the loop slipped during gait, the patient was at risk of bearing weight on the mending leg. Hallstedt recognized this limitation, and he designed a specialized shoe stirrup to minimize slippage. To make the stirrup, a first and second end of another shorter strap were riveted to opposite sides of the suspending U-shaped loop. The new loop comprised the stirrup, and the new loop formed into the stirrup was lodged forward of the heel of the shoe. However, the patient must wear the shoe to complement the stirrup. Without the shoe's heel, the stirrup was ineffective and the loop slipped. Thus, the stirrup will not work with a cast. The cast is smooth on the plantar side of the foot and does not provide a protruding heel. A cast boot or cast shoe that the patient might wear was not designed with the protruding heel needed to effectively work with the shoe stirrup. Thus, the Leg sling For Treatment of Unilateral Leg Diseases remained an ineffective device for improving the mobility of the patient wearing the leg cast. Further, those skilled in the art, namely Podiatrists and Orthopedic surgeons, have not recognized the Leg Sling For Treatment of Unilateral Leg Diseases as an effective and safe post surgical device to improve the patient's mobility following surgeries that require the leg cast and a period without weight bearing, such as a bunion correction where the first metatarsal bone of the great toe must be surgically severed, straightened, and re-positioned. Second, the issue of the patient's safety was not considered in the design since the patient had no means to instantly, effortlessly break apart the Leg Sling For Treatment of Unilateral Leg Diseases to prevent a potential fall with the assistance of the injured leg. Third, to prepare the sling apparatus for use from a sitting position, the patient had to lift the leg and insert the foot through the suspending loop. Once the loop was positioned around the shank of the leg, the specialized shoe stirrup was positioned underneath the heel of the shoe. This process was awkward, time consuming, and difficult in cramped conditions such as the driver's seat of a vehicle.

U.S. Pat. No. 5,882,321, Leg Sling and Abdominal Belt, Fisk (1999), provided another ambulatory leg sling, but a sling designed to accommodate the cast. As seen from the drawings of this prior art, the leg is suspended in a near vertical position with the suspended foot slightly to the rear of the other leg. An abdominal belt was provided to distribute the load of the suspended leg about the patient's lower torso placing the burden of the load on the hips of the patient. Shoulder straps were included to prevent the upper leading edge of the abdominal belt from rolling and slipping downward. As stated in the claims, the leg sling provided the U-shaped loop in which the sole of the suspended foot contacted the foot receiving means. The upper ends of the U-shaped loop could be anchored at a plurality of potential locations on the abdominal belt.

U.S. Pat. No. 5,882,321 had several shortcomings. First, the sling did not provide a means to instantly, effortlessly break apart to prevent a potential fall with the assistance of the injured leg. Second, similar to Hallstedt's Leg sling For Treatment of Unilateral Leg Diseases, the loop remained the means of suspension, and the sole of the foot rested in the bottom of the U-shaped loop. Third, while the suspended leg remained in a near vertical position, the load distribution carried by the abdominal belt remained more over the hip on the side of the suspended leg. Fourth, the leg sling apparatus required a considerable amount of time to completely remove and return to use. Fifth, the abdominal belt produced discomfort in a large patient, especially when sitting, by constraining the abdominal region.

Another device of the prior art is U.S. Pat. No. 5,911,696, Integral Strap Handling Device For A Leg Cast, Coates (1999). U.S. Pat. No. 5,911,696 provided a device for the patient to maneuver a cast, especially a heavy above-the-knee cast, about a bed or similar place of rest. The device was comprised of four straps. The instep strap crossed over the top of the forefoot; the complementing sole strap crossed underneath the sole of the foot. The heel strap crossed behind the heel of the foot. Two rings were used to bind the terminal ends of the three straps together. One ring bound the terminal ends on the lateral side of the ankle, and the other ring bound the terminal ends on the medial side. A means of adjusting the length of each strap was provided. Attached to the instep strap on the top of the forefoot was the assist strap, which provided a means for the patient to grasp the assist strap and maneuver the leg about while resting on the bed or sofa. However, the Integral Strap Handling Device For A Leg Cast did not provide a means to secure the foot apparatus to a load bearing means, and the position of the assist strap on the forefoot was of no value for this purpose. Further, there is no expressed or implied suggestion in this art to modify the Integral Strap Handling Device For A Leg Cast for other than its intended purpose, especially since it is a complete functional unit. However, even if necessary modifications were made to the Integral Strap Handling Device, to include removal of the assist strap and incorporation of an anchor means on the reward section of the heel strap, the Integral Strap Handling Device would produce an inferior result for distributing the forces about a user's foot while in a rearward, suspended state. In the rearward, suspended state, any anchor modified to fixedly attach to the heel strap must pull against the first and second rings on the sides of the foot with a force equal to the weight of the load, and all forces born by the suspended foot would be transferred through these two rings and about the band encircling the forefoot which is comprised only of the instep and sole straps. With only the forefoot completely encircled, the constant pressure applied at this one location would increase the user's discomfort since all forces born by the foot would be distributed about this single location. For a user wearing only a bandage covering the foot, this would be quite discomforting. Furthermore, the assist strap could snag an object during the ambulation cycle and cause a fall; removal of the assist strap would but be necessary to improve the user's safety but would render the Integral Strap Handling Device inoperable for its intended purpose.

Another device of the prior art is U.S. Pat. No. 3,739,772, Resilient Harness Device For A Walking Cast, Ennis (1973). The apparatus was comprised of a body harness adapted to extend diagonally across the user's torso depending from the user's shoulder on the side opposite the leg cast. Attached to a holding member at the terminal ends of the body harness strap was the first end of a lead strap. A second holder member was fixedly attached to the second end of the lead strap. Engaged to the second holding member on the lower end of the lead strap was a swivel eye spring connector attached by its releasable end. The other non-releasable end of this swivel eye spring connector was fixedly attached to the first distal end of a pull spring; the second distal end of the pull spring was fixedly attached to a second swivel eye spring connector by its non-releasable end. The releasable end of the second swivel eye spring connector was engaged to a holding member on a foot band encircling the forefoot of the walking cast. Adapted to the user, the lead strap was forward of the user's body. When the walking cast was in contact with the ground, the spring was stretched and potential energy stored. During the next forward step of the ambulation cycle, the spring assisted the patient with lifting the leg and cast thereby reducing the strain on the muscles of the leg. During this portion of the ambulation cycle, the load was distributed onto the user's shoulder. In order to modify the Resilient Harness Device For A Walking Cast to a functional ambulatory leg sling, numerous modifications would be necessary. However, there exists no suggestion in this art, expressed or implied, to modify the Resilient Harness Device For A Walking Cast into a functional leg sling. Assuming the minimal necessary modifications are performed, these modifications necessitate removal of the spring, removal of one swivel eye spring connector, reversal of the remaining swivel eye spring connector to orient the releasable end at the lower end of the lead strap, incorporation of a lead strap length adjustment means, and incorporation of a pad into the body harness to improve the user's comfort and mitigate the pressure on the shoulder. However, even if these modifications were made, the single foot band would produce an inferior result when suspending the leg. The use of the single band would increase discomfort when the leg was suspended for long periods, especially for the user with only a bandage covering the foot. With only the single band encircling the forefoot, the constant pressure applied at one location would increase discomfort since all forces born by the elevated foot are distributed about the single location. Further, these modifications would render the Resilient Harness Device For A Walking Cast inoperable for its intended function.

Another device of the prior art is U.S. Pat. No. 5,860,944, Hoffman, Jr. (1999). Hoffman, Jr. disclosed the Back Support Apparatus that essentially included a pair of shoulder straps, a waist belt, two guide tubes, a pair of heel connectors, a pair of support lines, and a pair of coil springs integrated into each of the support lines. The Back Support Apparatus assists the user with back support as an aid in performing manual labor requiring frequent bending from the waist. Adapted to the user, each support line was engaged to a heel connector attached to the user's feet; each heel connector was configured to couple with the respective heel of the shoe on each foot. Fixedly attached to each heel connector was a connection eye similar in design to an eyebolt. The connection eye was fixedly attached to the heel connector on the upstanding heel brace with the connection eye oriented upward and in line with the attached support line. The lower end of the wire rope support line was fixedly attached by a loop formed from the wire rope passing through the connector eye and then secured to itself with a suitable clamp. As designed, the connector eye was a rigid, non-pivotal anchor for securing the support line; the opposite end of each support line was adapted to the user's shoulders through the shoulder straps. Two straps with hook and loop fastener were included on each heel connector for snugly securing the heel connector to the user's shoe. If the heel connector is integrated as a foot receiving means into an ambulatory leg sling, the patient must wear a shoe since the heel connector is configured to couple with the respective heel of the user's shoe. A cast is typically wider than a shoe, and the upstanding heel brace would interfere with the cast properly seating into the heel connector. It would be necessary to expand the width of the heel connector to accommodate the cast; however, this would make the heel connector too large to snugly fit around a user's shoe or bandaged foot and thereby produce an inferior result. Although U.S. Pat. No. 5,860,944 does not state the material composition of the heel connector, the drawings suggest a rigid material such as a metal alloy or a hard plastic. In order to be an effective foot receiving means for an ambulatory leg sling, the foot receiving means must be adjustable in size to accommodate either a cast or a bandaged foot and be flexible to enhance comfort; the heel connector described does not afford these benefits. Further, the wire rope integrated into the support line and fixedly attached by loop and clamp to the eye connector must be removed from the heel connector, and removal of the wire rope would render the heel connector inoperable for its intended function. Yet, even if these modifications were performed, the heel connector would produce an inferior result for suspending the leg because of the force distribution problems described previously when the forces are distributed about a single location on the foot. And, the heel connector would not comfortably, securely remain on the foot during extended periods of bed rest due to its hard material structure and limited means of being secured to the shoe. Thus, the heel connector would not provide a suitable foot receiving means for the ambulatory leg sling.

BRIEF SUMMARY OF THE INVENTION

In accordance with the present invention, the Breakaway Leg Sling is provided comprising: a load bearing means provided by a torso harness device equipped with a single anchor ring; a soft, flexible foot receiving means provided by a separable foot cradle device equipped with a single anchor ring; a load transfer means provided by a load strap used to engage the single anchor of the foot receiving means to the single anchor of the load bearing means; a means to provide the patient immediate use of the injured leg in order to regain balance and prevent a fall provided by the breakaway safety fastener incorporated into the length of the load strap. Integrated into the Breakaway Leg Sling, these components provide a secure, safe, ergonomic leg suspensory system for use with the walker or crutches that lifts and suspends the single leg in a rearward, elevated position during the transition of standing from a seated position. The apparatus provides ample security from weight bearing while in the motion of standing, while in the sitting motion, or during the ambulation cycle. The apparatus provides a means to break apart using the breakaway safety fastener thereby providing the patient immediate use of the injured leg to prevent a fall and regain balance in the event of a trip or other loss of balance. And, the threshold of force required to open the breakaway safety fastener is sufficiently above the load of the suspended leg to provide the patient all of the advantages of the Breakaway Leg Sling during normal, routine use without the fastener accidentally opening. Yet, the breakaway safety fastener opens immediately when a sufficient pre-determined force is exerted on the safety fastener, such as the force exerted during the initial stage of a loss of balance. For patients ranging in weight from one hundred to two hundred and fifty pounds, the target force for opening the breakaway safety fastener is approximately twenty pounds. In a rearward, elevated rest position, the load of the single leg of the patient typically ranges from six to twelve pounds in the defined weight range, which includes the weight of a cast or shoe. Thus, to disengage the breakaway safety fastener and release the injured leg, the patient must exert a force on the load strap equal only to the difference between the opening force of the breakaway safety fastener and the force exerted on the breakaway safety fastener by the mere load of the suspended, rearward at rest leg. Those skilled in the prior art of leg slings have not recognized the need or advantages associated with integration of the breakaway safety fastener into the sling assembly to prevent a potential fall. This invention solves this unrecognized problem and provides a secure means of encasing the cast, boot, or shoe with straps; the device provided for this means is the foot cradle device. Furthermore, the foot cradle device provides two complementing, integrated bands, i.e., the forefoot loop and the ankle loop. When adapted to the user's foot, both bands completely encircle the foot and ergonomically interface with the natural shape of the human foot to eliminate slippage and improve the distribution of the forces born by the foot over a larger surface area thereby enhancing the patient's comfort. In order to suspend the leg, the foot cradle device provides the anchor ring on the rearward side of the heel to engage the lower end of the load strap. The upper end of the load strap is engaged to the anchor ring on the torso harness device. Incorporated into the length of the load strap is the breakaway safety fastener. Integrated into the Breakaway Leg Sling, the torso harness device, the foot cradle device, the load strap, and the breakaway safety fastener provide many advantages for the patient. Those skilled in the art will appreciate the secure means of suspension and comfort afforded by this invention and the enhanced safety of the patient provided by the breakaway safety fastener.

OBJECTS AND ADVANTAGES

Accordingly, several objects and advantages of this invention are:
(a) an improved and comfortable ambulatory leg sling;
(b) a device for encasing the foot that eliminates slippage about a cast, shoe, or bandaged foot;
(c) a foot cradle device that better distributes the forces born by the suspended foot;
(d) a safer means to avoid weight bearing on the sole of the foot during the ambulation cycle with the walker or crutches and, if needed, permit the patient immediate use of the injured leg to regain balance;
(e) an improved quality of life for patients during convalescence;
(f) an expedient means of preparing the Breakaway Leg Sling for use;
(g) a simple method of preparing the Breakaway Leg Sling for use from the seated position;
(h) an apparatus that lifts the leg securely, safely during the standing motion;
(i) an apparatus that does not hamper the patient during the sitting motion;
(j) a torso harness that is easily removed after sitting;
(k) a cushioned torso harness device to enhance comfort on the patient's shoulder;
(l) a comfortable means to maintain the foot cradle device on the foot for extended periods of time while sitting, resting, or sleeping thereby leaving the foot cradle device anchor in a ready-to-connect position to minimize preparation time and effort;
(m) a low manufacturing cost.

In addition to the objects and advantages listed herein, further objects and advantages will become apparent from a consideration of the drawings and the ensuing description.

BRIEF DESCRIPTION OF THE SEVERAL VIEWS OF THE DRAWING

FIG. 1 is a left side perspective view of a patient with the Breakaway Leg Sling suspending the left leg.

FIG. 2 is a rear side perspective view of the patient with the Breakaway Leg Sling suspending the left leg.

FIG. 3 is a front side perspective view of the preferred embodiment of the foot cradle device.

FIG. 4 is a rear side perspective view of the preferred embodiment of the foot cradle device.

DETAILED DESCRIPTION OF THE INVENTION

Description of Figures

Figure 5:
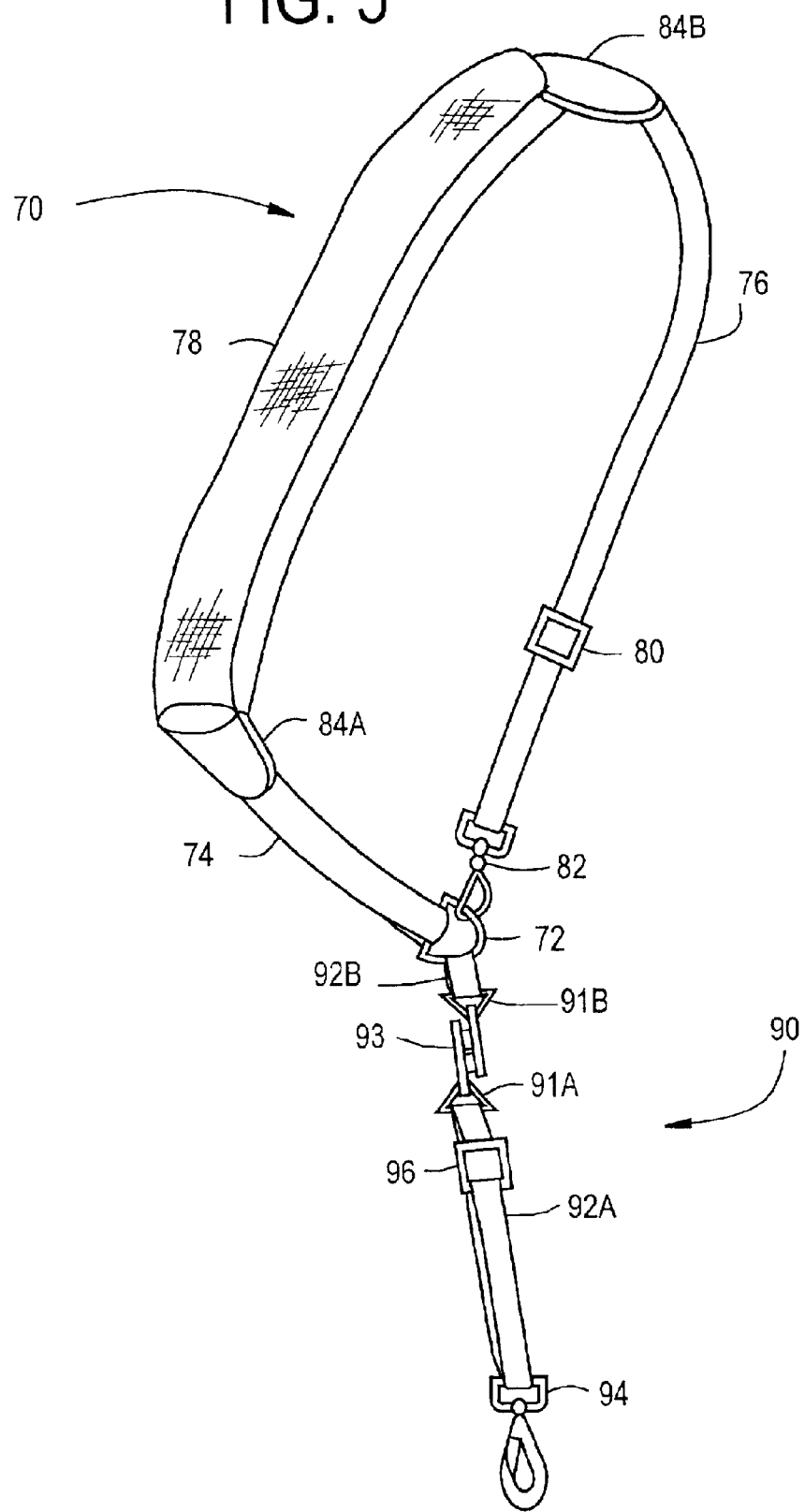
FIG. 5 is a side perspective view of the preferred embodiment of the torso harness device and the preferred embodiment of the load strap.

Reference is first made to FIG. 1 and FIG. 2, which illustrate the preferred embodiment of the invention. The Breakaway Leg Sling is comprised of three integrated assemblies consisting of the foot cradle device 20, the load strap 90, and the torso harness device 70. The torso harness is the load bearing means, and the foot cradle device is the foot receiving means. The load strap is the load transfer means used to integrate the load bearing means with the foot receiving means. Opposite ends of the load strap connect to the anchor ring 32 on the foot cradle device and to the anchor ring 72 on the torso harness device, and the breakaway safety fastener 93 is incorporated into the length of the load strap 90. As illustrated, the anchor 72 on the torso harness resides at the bottom of the torso harness loop, and the anchor 32 on the foot cradle device resides approximately along the axis of the Achilles tendon. It will be appreciated by those skilled in the art that the foot cradle device provides for ease of applying and removing, as well as a secure, customized fit.

Preferred Embodiment of the Foot Cradle Device

Referring now to FIG. 3 and FIG. 4, front and rear perspective views of the foot cradle device 20 are provided. As illustrated, the foot cradle device 20 is comprised of a forefoot loop 22, an ankle loop 24, a forefoot-connector loop 26, a plantar strap 28, the anchor ring 32, and a fold-down strap 34. A detailed description of each follows.

Referring to FIG. 3, three pieces of strap made of nylon webbing are fashioned into a loop, herein defined as the forefoot loop 22. To make the forefoot loop 22, a first strap, adapted to extend along the sole of the foot, is cut to length and opposite ends of the strap are secured by thread to the two double bar slides 42A and 42B on the side of each double bar slide incapable of adjustment. The two double bar slides 42A and 42B each provide one side capable of adjustment for the length of a strap; the remaining side of each double bar slide provides for fixedly attaching a strap to that end. The two straps 40A and strap 40B are cut to length and one end of strap 40A is secured by thread to annular ring 38; one end of strap 40B is secured by thread to annular ring 38. The secured ends of strap 40A and 40B are at opposite sides of the annular ring 38. The free end of strap 40A passes through the adjustable end of the double bar slide 42A; the free end of strap 40B passes through the adjustable end of the double bar slide 42B. When positioned on the patient's foot, the forefoot loop 22 provides the annular ring 38 residing on the top of the foot forward of the shank of the leg and the two double bar slides 42A and 42B integrated into the forefoot loop 22 on opposite sides of the annular ring 38. The circumference of the forefoot loop 22 is adjustable by pulling or pushing the free ends of strap 40A and 40B through the adjustable end of the double bar slide 42A and 42B.

A smaller loop, herein defined as the forefoot-connector loop 26, is attached to the annular ring 38. To fashion the forefoot-connector loop 26, a strap is first inserted through the ring 38, and the terminal ends of the strap are overlapped and secured by thread. Loop 26 should be of sufficient size to permit the strap comprising the ankle loop 24 with buckle 48 to slide through easily when the ankle loop 24 is disengaged. Referring to FIG. 4, on the plantar side of the foot centered opposite from the position of the annular ring 38 shown in FIG. 3 is the plantar strap 28. As illustrated in FIG. 4, the first end of the plantar strap 28 is secured by thread to the forefoot loop 22 at the seam 50. Both the annular ring 38 shown in FIG. 3 and the seam 50 shown in FIG. 4 lie approximately along an axis parallel to an imaginary line centered and extending down the length of the foot. As illustrated in FIG. 4, the plantar strap 28 extends from the seam 50 to the seam 60. At seam 60, the fold-down strap 34 is secured by thread to the plantar strap 28.

Referring to FIG. 3, the ankle loop 24 is fashioned from a detachable strap. The side release buckle 48, provided with a male end and female end for closing the buckle 48, is equipped with one adjustable end and one non-adjustable end. One end of the strap comprising the ankle loop 24 is fixedly attached to the non-adjustable end of the buckle 48; the opposite end of the strap passes through the adjustable end of buckle 48. Closing the buckle 48 forms the strap into the ankle loop 24. The end of the strap forming ankle loop 24 passing through the adjustable end of the buckle 48 provides the means of adjusting the circumference of the ankle loop strap 24 by pulling or pushing on this end of the strap. Thus, the patient may adjust the circumference of the ankle loop 24 to snugly encircle the ankle. Referring to FIG. 4, Integrated onto the strap forming the ankle loop 24, residing along the length of the strap between the terminal ends, is the anchor ring 32. The single bar slide 54 provides a means to maintain the anchor ring 32 in a stationary position on the ankle loop 24; yet, the anchor ring 32 is pivotal within the single bar slide 54 to a range of approximately 180 degrees. This pivotal capability of the anchor ring 32 permits the anchor ring to fold down and out of the way when the patient is wearing the foot cradle device 20 and resting the leg on a bed or similar surface. Furthermore, the patient may slide the anchor ring 32 and single bar slide 54 to alternate positions along the length of ankle loop 24. This provides the patient a means to position the anchor 32 on the rearward side of the heel along the axis of the Achilles tendon while custom fitting the foot cradle device 20. To place the anchor ring 32 and single bar slide 54 onto the strap, a free end of the strap comprising ankle loop 24 first passes through the single bar slide 54, then through the D-ring 32, and finally again through the single bar slide 54. Thus, the anchor ring 32 is integrated with the single bar slide 54, and the single bar slide 54 keeps the anchor ring 32 stationary unless the patient needs to adjust the position of the anchor ring 32 by sliding the anchor 32 along the length of the strap. Integration of the ankle loop 24 into the foot cradle device 20 is accomplished by inserting the strap comprising the ankle loop 24, after releasing the buckle 48, through the forefoot-connector loop 26. Thus, the ankle loop 24 is detachable from the other elements of the foot cradle device; the closure of the buckle 48 forms the ankle loop 24. The last element of the foot cradle device 20 is the fold-down strap 34. The fold-down strap 34 is secured to the plantar strap 28 such that equal lengths of the fold-down strap 34 extend from the seam 60. Referring to FIG. 4, at the first end of the fold-down strap 34 on the lateral side of the ankle, complementing hook and loop are sewn onto the strap 34 at location 58 to accommodate a fold. At the second end of the strap 34 on the medial side of the ankle, complementing hook and loop are sewn onto the strap 34 at location 56 to accommodate a second fold. To integrate the fold-down strap 34 into the foot cradle device 20, the first end is placed underneath the ankle loop 24 on the lateral side of the ankle; the first end is folded back and attached to itself using the complementing hook and loop sewn onto the strap 34 at location 58 thereby sandwiching the enclosed portion of the ankle loop 24 in the fold. The strap 34 extends from the first fold underneath the foot to the opposite ankle on the medial side. The second end of the strap 34 is inserted underneath the ankle loop 24 on the side opposite the first fold, and the second end of the strap 34 is folded back upon itself and attached to itself using complementing hook and loop sewn at location 56 thereby sandwiching the enclosed portion of the ankle loop 24 in the second fold. As seen in FIG. 4, where the fold-down strap 34 crosses over the plantar strap 28 on the plantar side of the foot, strap 28 and strap 34 are fixedly attached at seam 60.

Preferred Embodiment of the Load Strap

Again referring to FIG. 1, the load strap 90 provides the means to transfer the load of the suspended leg to the torso harness device 70. As illustrated in FIG. 5, the load strap 90 is comprised of the pivotal snap hook 94, an elongated strap 92A, a shorter elongated strap 92B, the double bar slide 96, and the breakaway safety fastener 93. Again referring to FIG. 1, one end of the load strap 90 is attached to the torso harness anchor ring 72; the opposite end of the load strap 90 provides the pivotal snap hook 94 to engage the anchor ring 32 on the foot cradle device 20. Again referring to FIG. 5, one side of the double bar slide 96 provides a means to adjust the length of the strap passing through the double bar slide 96; the remaining side of the double bar slide 96 provides a non-adjustable means for fixedly attaching the strap to that end. To fashion the load strap 90, one terminal end of the strap 92A is fixedly attached by thread to the non-adjustable side of the double bar slide 96. The opposite end of strap 92A first passes through the strap-holding member of pivotal snap hook 94. Then, the free end of strap 92A passes through the strap-holding member 91A located at one end of the breakaway safety fastener 93. Then the end of strap 92A passes through the adjustable end of the double bar slide 96. Thus, the strap 92A is formed into an adjustable loop, and the pivotal snap hook 94 and strap-holding member 91A of the breakaway safety fastener 93 reside at opposite ends of the elongated, adjustable loop. A second, shorter strap 92B passes through the torso harness anchor ring 72 and then through the strap-holding member 91B of the breakaway safety fastener 93; opposite ends of the shorter strap 92B are joined and secured by thread thus forming strap 92B into the loop shown in FIG. 5. Thus, the double bar slide 96 provides a means to adjust the length of the load strap 90; the breakaway safety fastener 93 provides a means for the patient to regain immediate use of the suspended leg, if necessary, to prevent a potential fall. During normal use, the pivotal snap hook 94 provides the means to engage the foot cradle device anchor ring 32, shown in FIG. 4.

Preferred Embodiment of the Breakaway Safety Fastener

Figure 6:
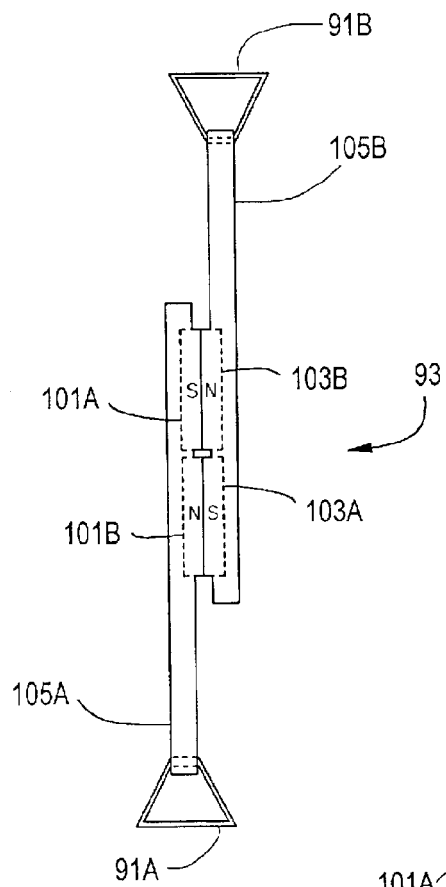
FIG. 6 is an enlarged perspective view of the breakaway safety fastener in a closed position.
Figure 7:
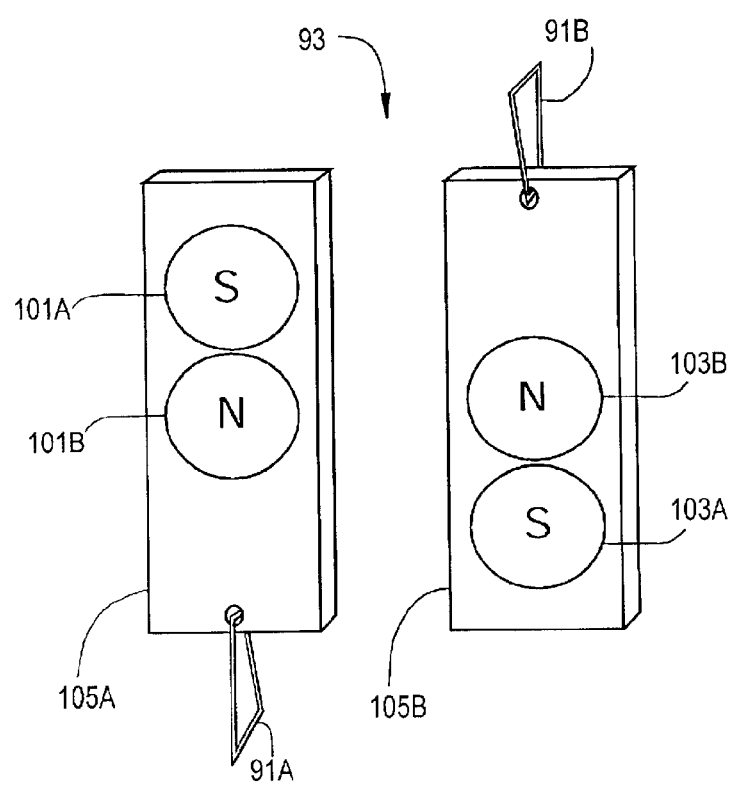
FIG. 7 is an enlarged perspective view of the breakaway safety fastener in an open position.

As illustrated in FIG. 5, the breakaway safety fastener 93 is incorporated into the length of the load strap 90. Referring to FIG. 6 and FIG. 7, an enlarged view of the breakaway safety fastener 93 is provided. To make the breakaway safety fastener 93, two equal lengths of ferrous-alloy plates are used. The approximate dimensions of the metal plates 105A and 105B are 1 inch by ¼ inch by 5 inches in width, thickness, and length. Two cylindrical cavities of equal depth are machine milled into the metal plate 105A; metal plate 105B is identical to plate 105A. As shown in FIG. 6 and FIG. 7, the cavities in housing member 105A and 105B are nearer one end of each plate than the other end; the distance from the proximal end to the nearest cavity measures approximately ¼ inch. Each cylindrical cavity is milled to an approximate depth in the thickness of each plate to permit a magnet to be recessed into each cavity; when recessed, the magnet protrudes slightly above the surface of the plate. The thickness of the wall separating the two cavities in the plate is approximately ⅛ inch as measured along an axis extending through the center of both cavities. A cylindrical rare earth magnet of a type known to the art measuring in diameter just less than the diameter of the cylindrical cavity is inserted into each of the cavities in the two plates 105A and 105B. The magnets are sintered neodymium iron boron disk magnets, and the north and south poles are on opposite sides and parallel to the thickness of each disk magnet. The use of the ferrous-alloy housing member for plates 105A and 105B precludes the need for bonding the magnets to the housing members and protects the sintered neodymium iron boron magnets from damage during closing of the fastener; the magnets remain recessed in their respective cavities during use. Alternate material embodiments of the housing members 105A and 105B, such as a plastic or a non-ferrous alloy material, require the magnets to be bonded or glued into their cavities. Each magnet disk measures approximately ¾ inch by ⅛ inch in diameter and thickness. All four magnets are of equal magnetic strength. In a magnetic pull test, the single disk magnet is sandwiched between two ¼ inch thick ferrous-alloy plates, and the two widest surfaces of the single disk magnet are in flush contact with the two separate metal plates. When the pull force is applied to one plate parallel to the thickness of the disk magnet and the second plate is held stationary, the force required to separate the two plates equals approximately fifteen pounds. As illustrated in FIG. 6, magnets 101A and 101B are inserted into the two cavities of the plate 105A; magnets 103A and 103B are inserted into the two cavities of the plate 105B. As illustrated in FIG. 7, magnet 101A and 101B provide opposite magnetic pole orientation relative to the plate 105A; magnet 103A and 103B provide opposite magnetic pole orientation relative to the plate 105B. This north-south orientation is illustrated in FIG. 6 and FIG. 7 where "N" represents the north pole of the magnet and "S" represents the south pole of the magnet; the poles are parallel to the thickness of the magnet disks. Thus, the two magnets in each plate 105A and 105B provide one magnet with a south pole orientation and one magnet with a north pole orientation, and complementing magnets in plate 105A and 105B attract each other when the plates 105A and 105B are coupled. Each coupled magnet pair between housing member 105A and 105B are coaxially located and in flush contact when the breakaway safety fastener 93 is in the closed position. Since the magnets protrude slightly above the surface plane of plate 105A and plate 105B, only the complementing magnets contact when the breakaway safety fastener 93 is coupled. And, coupled, the two sets of coaxially located magnet pairs in housing member 105A and 105B provide a substantially rigid, non-pivotal fastener such that the housing members 105A and 105B are substantially non-pivotal with respect to one another. The strap holding member 91A attached to the housing member 105A is at the distal end from its recessed magnets 101A and 101B; the strap holding member 91B attached to the housing member 105B is at the distal end from its recessed magnets 103A and 103B. The strap holding members 91A and 91B each are a brass triangle ring of a type known to the art that is opened, inserted through holes drilled through the distal ends of the plates 105A and 105B, and again closed. The strap-holding members 91A and 91B provide the means of incorporating the breakaway safety fastener 93 into the length of the load strap 90, as shown in FIG. 5. Opening or disengaging the breakaway safety fastener 93 requires a pull force of approximately twenty pounds applied longitudinally to the breakaway safety fastener 93.

An alternate embodiment of the breakaway safety fastener 93 envisions replacement of the four disk magnets with two bi-polar rectangular magnets; each rectangular magnet providing both a north and south pole parallel through the thickness of the magnet and at opposite ends on a single surface. The two housing members would require machine milling to provide complementing cavities in the two-piece housing for insertion of the recessed magnets. Coupled, opposite poles between the magnet pair would attract and provide a result similar to the preferred embodiment. Magnetic pull tests would be required to determine the correct size and strength of the magnet for this embodiment.

A second alternate embodiment of the breakaway safety fastener 93 contemplates the substitution of the ferrous-alloy with a non-ferrous alloy or plastic extrusion member. For example, each plate could be designed as a two-piece plastic extrusion component interlocking with snap-together pieces; the cavities for recessing the magnets could be formed into the plastic member, and an optional soft iron plate could be sandwiched between the joined pieces beneath the cavities and held stationary with plastic clips integrally formed in the plastic member. The magnets could be bonded to the iron plate or bonded to the plastic if the iron plate was not used. Other strap engaging means, such as accommodating slots in the distal ends of the fastener body, may be substituted for the strap holding member 91A and 91B. As in the preferred embodiment, the two finished housing members could be identical, and the magnets could be either disk or rectangular.

Preferred Embodiment of the Torso Harness Device

Referring to FIG. 1, the torso harness device 70 is the load bearing means. As illustrated in FIG. 5, the torso harness device includes both a front strap 74 and a rear strap 76. Other elements of the torso harness include a pad 78, a double bar slide 80, the single anchor ring 72, and a pivotal snap hook 82. As illustrated in FIG. 1, the pad 78 attached to strap 74 crosses over the shoulder on the side opposite of the suspended leg and extends onto the patient's front and rear torso areas. The front strap 74 and the rear strap 76 are attached to the anchor ring 72; anchor ring 72 resides at the bottom of the loop. Referring to FIG. 5, the elongated pad 78 is made of foam rubber, cotton wadding, or any other suitable type of padding material known to the art, and the foam rubber is encased with a fabric. As illustrated, strap 74 and strap 76 extend from opposite ends of the two narrowest sides of pad 78; the straps 74 and 76 are made of nylon webbing or any other suitable material. One end of the front strap 74 is attached to the lower end of the pad 78. The strap 74 extends around the side of the patient and is engaged to the torso harness anchor 72. The rear strap 76 extends from the upper end of the pad 78, diagonally across the patient's back, and is engaged to the anchor 72. As illustrated in FIG. 1, the anchor 72 is at the bottom of the loop formed when the terminal ends of the front strap 74 and the rear strap 76 are engaged to the anchor 72. Again referring to FIG. 5, at the two terminal ends of the pad 78 where the front strap 74 and the rear strap 76 are sewn to the pad 78, the fabric of pad 78 is lapped over the ends of each strap. Each strap is then secured by thread to the fabric. Each seam is sandwiched between two pieces of like leather herein defined as seam covers 84A and 84B. The seam covers 84A and 84B provide additional strength and reinforcement for each seam. The two like pieces of 84A and the two like pieces of 84B are stitched together wherein the stitching passes through the first piece of leather, through the strap and the fabric, and through the second piece of leather. To provide the rear strap 76 with a means to adjust the length, the double bar slide 80 is fashioned into the length of the strap 76.

Description of Operation

Referring to FIG. 1, the Breakaway Leg Sling of the instant invention is comprised, in sequential order, of the foot cradle device 20, the load strap 90, the breakaway safety fastener 93, and the torso harness device 70. As illustrated in FIG. 1, the secure holding members, defined as the anchors 72 and 32, are provided on both the torso harness device and the foot cradle device. The load strap 90 provides the load transfer means wherein the opposite ends of the load strap are engaged to the anchor 72 and the anchor 32. Integrated into the Breakaway Leg Sling, the foot cradle device 20, the load strap 90, the breakaway safety fastener 93 and the torso harness device 70 assist the patient with an effective, expedient, secure, and safe apparatus for weight avoidance on the suspended leg while using the walker or crutches.

The load strap 90 and the foot cradle device 20 are detachable from each other. The torso harness device provides the anchor ring 72, and the foot cradle device provides the anchor ring 32. Opposite ends of the load strap 90 are engaged to the anchor ring 32 on the foot cradle device 20 and the anchor ring 72 on the torso harness device 70. The breakaway safety fastener 93 is incorporated into the length of the load strap 90. The pivotal snap hook 94 attached to the lower end of the load strap 90 provides the means to engage or disengage the load strap to the anchor ring 32 during routine use. The anchor ring 32 is secure and fastened to the foot cradle device and positioned on the rearward side of the heel along the axis of the Achilles tendon. When the foot is suspended and elevated in a rearward position, the anchor ring 32 is at the highest point of elevation of the suspended foot. And, the foot cradle device may be left on the foot for extended periods of time, after removing the torso harness and load strap, thereby leaving the anchor ring 32 in the ready-to-connect position.

Referring to FIG. 3, the design of the foot cradle device 20 is such that, after custom sizing to fit the foot, the foot cradle device may be removed from the foot by releasing the single buckle 48 and replaced by closing the single buckle 48 without resizing the forefoot loop 22 or the ankle loop 24. When the patient removes the foot cradle device, the buckle 48 is released, and the forefoot loop 22 is slipped off of the foot. The strap of the ankle loop 24 is left in position passing through the forefoot-connector loop 26. To return the foot cradle device to the foot, the forefoot loop 22 is slipped onto the forefoot and into position. The medial side of the fold-down strap 34 is temporarily disengaged, and the buckle 48 on the ankle loop 24 is fastened. The fold-down strap 34 is pulled taunt and fastened again. Thus, removal or replacement is accomplished in a matter of seconds thereby providing the patient a means to easily remove the foot cradle device to accommodate usage of a bandage or cast protector while bathing.

Referring to FIG. 3, initially, the patient must customize the fit of the foot cradle device. The forefoot loop 22 is customized to fit the patient with the adjustable strap ends 40A and 40B passing through the adjustable ends of double bar slides 42A and 42B. To position the forefoot loop 22 on the patient, the toes are first inserted through the forefoot loop 22. The annular ring 38 integrated into the forefoot loop 22 is positioned on the top center of the forefoot, and the forefoot loop 22 is pulled onto the forefoot and brought to rest just forward of the shank of the leg. The forefoot loop 22 should be adjusted to fit comfortably snug in this position. Next, the patient adjusts the length of the strap provided for the ankle loop 24 at the adjustable end of the buckle 48 in order to adjust the circumference of the ankle loop 24; the ankle loop 24 is equipped with the buckle 48 for closing the strap into the ankle loop 24. To position the ankle loop 24, the patient opens buckle 48 and pushes a free end of the strap comprising the ankle loop 24 through the forefoot-connector loop 26. The male and female portions of the buckle 48 are closed, and the ankle loop 24 is now positioned about the ankle. The forefoot-connector loop 26 and the fold-down strap 34 provide the means for integrating the forefoot loop 22 and ankle loop 24, and the complementing comfortably snug positions of the forefoot loop 22, the ankle loop 24, and the fold-down strap 34 eliminate slippage of the foot cradle device along the foot or leg and improve the distribution of the forces born by the foot while in the suspended state. Since the ankle loop 24 passes through the forefoot-connector loop 26 but is not fixedly sewn to other elements of the foot cradle device 20, the buckle 48 remains positional about the ankle. Positioned correctly, the buckle 48 will reside on the medial side of the ankle to provide the patient easy access. The patient will appreciate this ergonomic feature since the buckle 48 is much easier to access on the medial side of the ankle. In addition, the positional capability of buckle 48 allows the manufacture of a single foot cradle device for use with either the right or the left foot. Referring to FIG. 4, while customizing the fit, the patient slides the anchor ring 32 incorporated into the single bar slide 54 to its functional position on the rearward portion of the heel along the axis of the Achilles tendon.

The fold-down strap 34 is the final strap adjustment on the foot cradle device 20. To position the fold-down strap 34, one end of the strap 34 is placed underneath the ankle loop 24 on the lateral side of the ankle; this end of the fold-down strap 34 is then folded down and attached to itself with the complementing hook and loop sewn onto the fold-down strap 34 at location 58. The fold-down strap 34 extends from the ankle on the lateral side underneath the foot and back up to the ankle on the medial side. The second end of the fold-down strap 34 is then placed underneath the ankle loop 24 on the medial side of the ankle. The second end is folded and attached to itself with the complementing hook and loop sewn onto the fold-down strap 34 at location 56. The ankle loop 24 is thereby sandwiched into the folds of the fold-down strap 34 on both the lateral and medial sides of the ankle. The snug position of the fold-down strap 34 pulls downward on the ankle loop 24 and keeps the ankle loop 24 from slipping along the shank of the leg.

Referring to FIG. 5, the torso harness device also requires initial adjustment to best fit the patient. The torso harness device was fashioned into the loop by engaging the strap 74 and the strap 76 to the anchor ring 72. The desired circumference of the loop formed by the straps 74 and 76 is obtained using the double bar slide 80. Referring to FIG. 1, the patient places the head through the torso harness loop and the loop depends from the shoulder on the side opposite of the suspended leg; the load strap drops into position naturally. The pad 78 extends over the top of the shoulder onto the front and rear areas of the patient's torso. The anchor ring 72 hangs alongside the hip on the side of the leg to be suspended, and the straps 74 and 76 cross diagonally the front and rear sides of the torso. At the lower end of the load strap 90 is the pivotal snap hook 94 used to engage the load strap to the anchor 32. The double bar slide 96 is provided to adjust the length of the load strap 90 to accommodate differences in height or change the angle of elevation of the suspended leg.

Referring to FIG. 1, the patient places the torso harness device 70 in place as described from the seated position. The patient now engages the pivotal snap hook 94 on the lower end of the load strap 90 to the anchor ring 32. The patient stands on the good leg with the assistance of the walker or crutches, and the natural motion of standing pulls the leg securely in a rearward, elevated position. A more comfortable distribution of the load is achieved by using the muscles of the suspended leg to lift the leg slightly upward thereby relaxing the tension in the torso harness device 70. With the tension in the torso harness temporarily relieved, the patient grasps the pad 78 on the front torso and rotates the pad slightly downward about its axis. This motion repositions the torso harness anchor ring 72 more rearward and behind the buttock and improves the load distribution, and the comfortable distribution of the load is achieved. The suspended leg is now fully relaxed, and the patient is ready for the ambulation cycle.

Following the custom sizing, the patient may leave the foot encased by the foot cradle device 20 without hampering comfort. Wearing the foot cradle device leaves the anchor ring 32 in the ready-to-connect position and shortens preparation time before ambulation. The torso harness device 70, with the load strap 90 attached to the anchor ring 72, will generally be removed from the patient's body whenever the patient is sitting or lying down.

To assure security from weight bearing during the sitting motion, the patient first prepares to sit with the patient's back facing the chair or sitting surface. Then, while standing with the aid of the walker or crutches, the patient lifts the suspended leg slightly upward with the muscles of the leg thereby relaxing the tension in the torso harness device 70. With the tension relaxed, the patient can easily move the suspended leg forward of the body. The torso harness loop easily turns about its axis, and the torso harness anchor ring 72 moves forward alongside the hip. The load strap 90, still engaged to the anchors 72 and 32, limits the arc of the swing and prevents the foot from contacting the ground. With the leg now forward of the vertical line of the body, the patient comfortably, safely sits.

The use of the Breakaway Leg Sling during the ambulation cycle is simple. With the leg held in its suspended state and the load distribution comfortably adjusted using the method and manner described, the patient leans slightly forward from the waist. While in this position, the patient transfers the weight of the body into the hands while gripping the handles of the walker or crutches. With the weight of the body transferred into the handles, the patient lifts the good leg, and the good leg swings forward. Balance is facilitated during this motion because the load of the suspended leg is distributed into the upper central torso of the patient. With slippage of the foot receiving means eliminated, the Breakaway Leg Sling provides the patient with security from weight bearing during ambulation.

The breakaway safety fastener 93 incorporated into the length of the load strap 90 remains in a closed position during the patient's normal use of the Breakaway Leg Sling. The patient uses the pivotal snap hook 94 to engage or disengage the anchor ring 32 for suspending or releasing the leg. In the event the patient loses balance while using the walker or crutches, the breakaway safety fastener 93 provides the patient immediate use of the suspended leg for regaining balance. Thus, the released leg may be used and placed on the ground if necessary, and this action facilitates the patient's ability to regain balance and avoid a potential fall. This unique safety fastener requires no adjustment before use. The force exerted on the closed fastener required to open the fastener and release the suspended leg is approximately twenty pounds. For the patient ranging in weight from one hundred to two hundred and fifty pounds, this force is easily obtained. It is contemplated that patients outside of this weight range may require a breakaway safety fastener 93 opening at a different target force, but construction of a safety fastener to accommodate the patients outside of the defined weight range is easily accomplished by incorporation of weaker or stronger magnets into housing body of the safety fastener. In the event that the breakaway safety fastener 93 opens to release the suspended leg, the patient restores the breakaway safety fastener 93 to its functional, closed position by bringing the two separated parts of the safety fastener housing into close proximity; the magnet orientations are such that the two separate parts of the fastener housing will align and snap closed. This is accomplished in a matter of seconds, and the patient is then able to immediately resume use of the Breakaway Leg Sling after restoring the breakaway safety fastener 93 to the closed position.

Scope and Ramifications

It will be apparent to those skilled in the art that various modifications and variations can be made into the system and method of the present invention without departing from the spirit or scope of the invention. Thus, it is intended that the present invention cover these modifications and variations provided they come within the scope of the appended claims and their equivalents. Several alternate embodiments of the ambulatory sling apparatus were identified in the parent application and others contemplated include substitution of different types of strap material such as nylon, leather, or the like known to the art, or substitution of different types of web strap adjustment members or holding members such as web slides, web strap locks, pivotal snap hooks, snap hooks, side release buckles, center release buckles, and the like known to the art, or substitution of different shapes of rings such as D shape rings, triangle rings, annular rings, and the like known to the art, or substitution of different types of material composition for the adjustment members, the holding members, and the rings such as plastic, metal, or the like known to the art, or substitution of fewer but stronger magnets into the fastener housing to achieve the benefits of the breakaway safety fastener, or substitution of different sized or different shaped magnets to achieve the benefits of the breakaway safety fastener, or substitution of bi-polar magnets for the conventional pole magnets to achieve the benefits of the breakaway safety fastener.

What is claimed is:

1. An apparatus for use with a walker or crutches to suspend a single leg of a human user bent at the knee in a rearward elevated position while standing on the other leg to avoid weight bearing comprising:

a.) a foot cradle device providing means for receiving a foot, equipped with a first anchor ring and adapted to engage the user's foot, said foot cradle device surrounding the forefoot and ankle of a user, and said first anchor ring residing on the rearward portion of a user's heel, approximately along the axis of the Achilles tendon;

b.) a torso harness device providing means for load bearing, equipped with a second anchor ring;

c.) a load strap providing a means for load transfer, with a first end and a second end, wherein during use the first and second ends of said load strap engage said first anchor ring of said foot cradle device and said second anchor ring of said torso harness device;

d.) a breakaway safety fastener incorporated into the length of said load strap, providing means for disengaging at a pre-determined load whereby a user can release a suspended leg using the muscles of the suspended leg while standing on the user's other leg, wherein said breakaway safety fastener comprises two magnets of opposite polarity.

2. The apparatus of claim 1, wherein said breakaway safety fastener disengages at an effective pre-determined load in excess of the load exerted on said breakaway safety fastener by the load of the user's rearward, elevated leg.

3. The apparatus of claim 1, wherein said foot cradle device further comprises:

a.) a first closed loop formed from a first flexible, elongated member, with means for adjusting the circumference of said first closed loop, and adapted to engage the user's foot such that said first closed loop completely encircles the user's forefoot forward of the shank of the leg;

b.) a second closed loop formed from a second flexible, elongated member with means for adjusting the circumference of said second closed loop, and adapted to engage the user's foot such that said second closed loop completely encircles the user's ankle approximately at the shank of the leg;

c.) means for integrating said first closed loop with said second closed loop of said foot cradle device;

d.) wherein said second closed loop is equipped with a releasable fastener;

e.) wherein said first anchor ring of said foot cradle device is integrally attached to said second closed loop;

f.) and said first anchor ring is pivotal within a plane of approximately 180 degrees.

4. The apparatus of claim 1, wherein the breakaway safety fastener comprises for disengaging at a pre-determined load wherein the forces applied to said fastener are pull forces applied longitudinally to said fastener body, wherein said means for disengaging comprise:

a.) a first housing member with a first strap holding member;

b.) a second housing member with a second strap holding member;

c.) one or more magnets fixedly attached to said first housing member;

d.) one or more magnets fixedly attached to said second housing member;

e.) wherein said magnets fixedly attached to said first housing member are of an equal number to said magnets fixedly attached to said second housing member;

f.) wherein said magnets attached to said first housing member and said complementing magnets attached to said second housing member are in opposite magnetic pole orientation whereby said magnets attached to said first housing member are attracted to said complementing magnets attached to said second housing member;

g.) wherein when coupled said fastener provides said magnets in said first housing member in flush coaxial contact with said magnets in said second housing member.

5. The apparatus of claim 4, wherein when coupled said first housing member and said second housing member are substantially rigid and non-pivotal.

6. The apparatus of claim 4, wherein when coupled said first strap holding member and said second strap holding member are substantially at opposite distal ends of the fastener body.

7. The apparatus of claim 4, wherein when coupled said forces applied longitudinally to the fastener body to disengage said fastener are applied at said first strap holding member and said second strap holding member.

* * * * *